(12) United States Patent
Hipolito et al.

(10) Patent No.: US 6,668,832 B2
(45) Date of Patent: Dec. 30, 2003

(54) ENDOTRACHEAL TUBE

(75) Inventors: Ronaldo B. Hipolito, Stockton, CA (US); Michael P. Sherman, Davis, CA (US); Jay M. Milstein, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/040,982

(22) Filed: Dec. 28, 2001

(65) Prior Publication Data

US 2003/0121521 A1 Jul. 3, 2003

(51) Int. Cl.$^7$ .............................................. A61M 16/00
(52) U.S. Cl. ............................ 128/207.14; 128/200.24
(58) Field of Search ...................... 128/207.14, 207.15, 128/207.18, 200.26, 207.17, 912, DIG. 26, 200.24, 205.23; 116/280, 307, 308, 311–315, 318, 319; 600/19, 23, 28, 45, 93.01, 96.01, 100.01

(56) References Cited

U.S. PATENT DOCUMENTS

| | | | | |
|---|---|---|---|---|
| 3,508,554 A | * | 4/1970 | Sheridan ................ | 128/207.14 |
| 4,344,428 A | * | 8/1982 | Sherman ................ | 128/207.14 |
| 4,502,482 A | * | 3/1985 | DeLuccia et al. ...... | 128/207.15 |
| 4,567,882 A | * | 2/1986 | Heller .................... | 128/207.14 |
| 4,774,943 A | * | 10/1988 | Yu .......................... | 128/207.14 |
| 5,263,478 A | | 11/1993 | Davis | |
| 5,507,284 A | * | 4/1996 | Daneshvar ............. | 128/207.14 |
| 5,623,924 A | * | 4/1997 | Lindenman et al. ... | 128/207.17 |
| 5,873,362 A | | 2/1999 | Parker | |
| 5,941,816 A | * | 8/1999 | Barthel et al. .......... | 600/120 |
| 6,053,166 A | * | 4/2000 | Gomez .................. | 128/200.26 |
| 6,149,603 A | * | 11/2000 | Parker ................... | 600/532 |

OTHER PUBLICATIONS

Kuhns, et al., "Endotracheal Tube Position in the Infant," *The Journal of Pediatrics*, vol. 78, No. 6, pp. 991–996, (Jun. 1971).

Loew, et al., "A New and Safe Method to Control the Depth of Endotracheal Intubation in Neonates," *Pediatrics*, vol. 54, No. 4, pp. 506–508, (Oct. 5, 1974).

Thibeault, et al., "Pulmonary Interstitial Emphysema, Pneumomediastinum, and Pneumothorax," *Am J Dis Child*, vol. 126, pp. 611–614, (Nov. 1973).

Tochen, "Orotracheal Intubation in the Newborn Infant: A Method for Determining Depth of Tube Insertion," *The Journal of Pediatrics*, The C.V. Mosby Company, pp. 1050–1051, (Dec. 1979).

"Pediatric Research," *Pediatric Academic Societies Annual Meeting, Saturday, Apr. 28—Tuesday, May 1, 2001,Program Issue*, vol. 49, No. 4, Part 2 of 2, Baltimore Convention Center, Baltimore, Maryland, 4 pages, (Apr. 2001).

* cited by examiner

Primary Examiner—Weilun Lo
Assistant Examiner—Teena Mitchell
(74) Attorney, Agent, or Firm—Townsend and Townsend and Crew LLP (57) ABSTRACT

An endotracheal tube and a method for using an endotracheal tube are disclosed. In one embodiment, the endotracheal tube includes a tubular member including a distal end and a proximal end. The endotracheal tube also includes a plurality of visually distinct regions that is closer to the proximal end than the distal end. Each visually distinct region is spaced from other visually distinct regions, and each of the distinct region comprises a respectively different color.

15 Claims, 5 Drawing Sheets

ENDOTRACHEAL TUBE

CROSS-REFERENCES TO RELATED APPLICATIONS

Not applicable.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Endotracheal intubation is a common medical procedure. Endotracheal tubes are used in many situations. They are used as conduits for airway life support where patients have stopped breathing on their own (e.g., because of cardiac arrest, respiratory distress/arrest, seizures, and the like). They are also used in both human and animal surgery to provide passageways for anesthetic gases into lungs.

Endotracheal tubes are typically made of soft biomaterials. The most common biomaterial is polyvinyl chloride with a plasticizer added, but other synthetic materials are either currently used or are being developed. The endotracheal tube made of this soft material is difficult to manipulate and insert into the trachea (windpipe). A malleable stylette is often placed into a central lumen of an endotracheal tube to provide more rigidity to the tube and allow the caregiver to have better control during the tube's insertion. In practice, the added stiffness allows the caregiver to easily guide the distal end of the endotracheal tube between vocal cords and into a patient's trachea. Typically, such stylettes are malleable rods made of plastic or a plastic-coated soft metal. Normally, the stylette is inserted the length of the endotracheal tube's central lumen to a point just before the endotracheal tube ends. After the endotracheal tube is inserted into the trachea, the stylette is immediately removed.

Typically, the oral insertion of an endotracheal tube occurs while the patient lies on the back and the neck is slightly extended with the nose in a sniffing position. A caregiver, using his left hand to hold a laryngoscope, inserts the laryngoscope into the right corner of the mouth and advances its tip to the depth of the esophagus (swallowing tube into the stomach). The caregiver uses the laryngoscope to displace the tongue to the left side of the mouth, out of the way and providing a line-of-sight into the deepest portion of the patient's throat. This line-of-sight extends into the patient's esophagus, which is a large, wide, funnel-shaped structure. The laryngoscope is withdrawn from the esophagus until the patient's epiglottis and vocal cords (which define an entrance into the patient's trachea) come into view. The epiglottis and the vocal cords lie in front of and above the esophagus. The caregiver then inserts the distal end of the endotracheal tube through the vocal cord opening and into the trachea. After the endotracheal tube is properly positioned in the patient's trachea, the tube is secured to the patient's lip (e.g., with tape or a device).

The caregiver cannot see the distal end of an endotracheal tube after it has been inserted through the vocal cords. Consequently, it is difficult to determine the ultimate depth of insertion. Thus, the caregiver uses a reference mark on the tube that can be seen inside the mouth and that indicates the proper depth of insertion. Also, during prolonged periods of intubation that provide assisted breathing, it is difficult to tell if the endotracheal tube has moved from its initial, secured position. Inserting an endotracheal tube too far into the patient can be hazardous. For example, if an endotracheal tube extends beyond the carina (i.e., the point at which the trachea branches into the right and left lung) and into the patient's right mainstem bronchus, the bronchial intubation can result in injury.

Right mainstem bronchial intubation (RMSBI) can cause the complications listed below or even death of the patient. This is especially true with respect to small patients such as neonates. RMSBI is a potential cause of morbidity during neonatal assisted ventilation (breathing). RMSBI can cause overdistention of the right middle and/or lower lobes of the lung and underventilation and/or atelectasis of the remaining lung (cited in Kuhns L. R. and Poznanski A. Endotracheal position in the infant. *J Pediatr* 1971;78:991–6; Kattwinkel J. *Textbook of Neonatal Resuscitation*. 4th ed., Elk Grove Village: American Academy of Pediatrics and American Heart Association; 2000, p. 5–27). If inflation of a pulmonary lobe is excessive, lobar emphysema, pulmonary interstitial emphysema, pneumothorax, and/or pneumomediastinum may occur (cited in Thibeault D. W., Lachman R. S., and Kwong M. S. Pulmonary interstitial emphysema, pneumomediastinum, and pneumothorax in the newborn infant. *Am J Dis Child* 1973;126:611–4).

Figure 1:
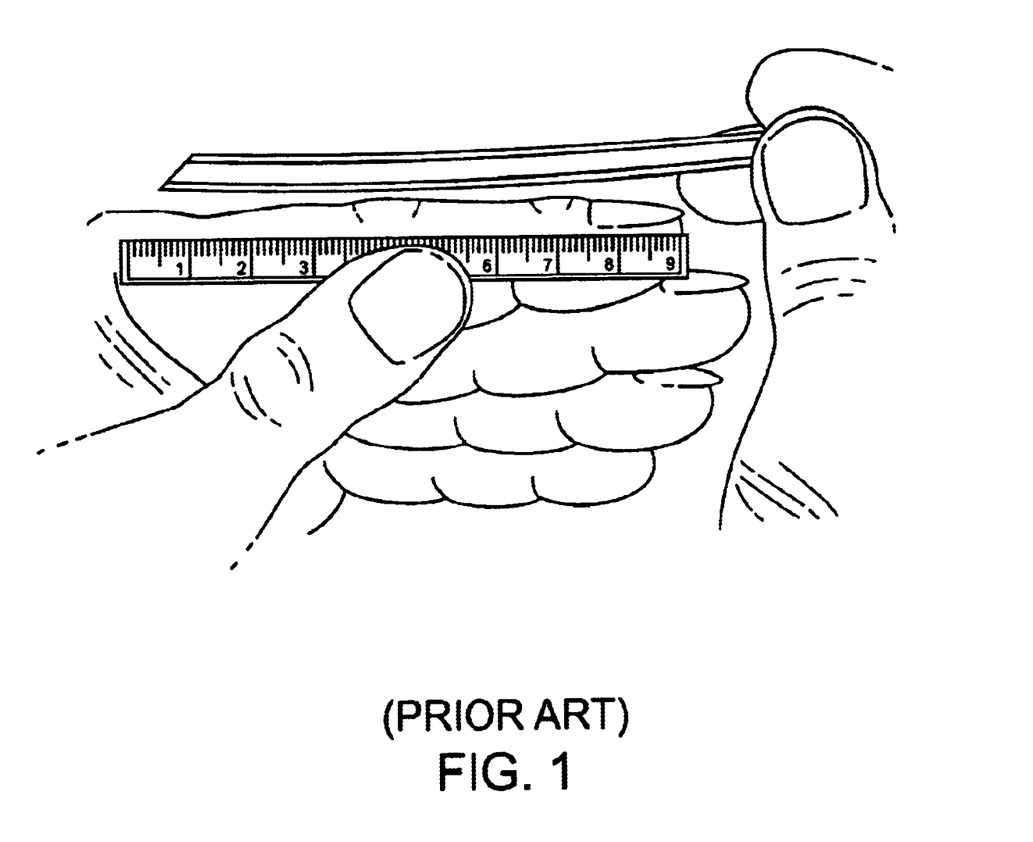
FIG. 1 shows a side view of a portion of an endotracheal tube that is suitable for use with an infant.

The risk of RMSBI in neonates is high relative compared to larger patients because the distance from the larynx (vocal cords) to the carina is relatively reduced in newborn infants. The endotracheal tubes that are used for intubation of newborn infants are also smaller than those used with larger patients. FIG. 1, for example, shows the tubular portion of an endotracheal tube. The tubular portion shown in FIG. 1 has a length on the order of an adult finger. If the patient has a weight of, for example, 1 to 2 pounds, the acceptable positioning of the distal end of the endotracheal tube within the trachea may only be an up and down distance of about 0.25 to 0.5 inches. Thus, the margin for error when inserting and maintaining an endotracheal tube in neonates is especially small.

Today, more extremely low birth weight infants (<1000 g) are treated with assisted ventilation. As medical technology continues to improve the survival rate of preterm neonates, there is a need to reduce the problems associated with endotracheal intubation in preterm and term newborn infants. There is also a need to reduce the problems associated with intubation of other patients such as toddlers and adults.

Accordingly, improved endotracheal tubes and methods for using the same would be desirable. Embodiments of the invention address the above noted problems and other problems, individually and collectively.

SUMMARY OF THE INVENTION

Embodiments of the invention relate to endotracheal tubes and methods for using endotracheal tubes. The endotracheal tubes may be adapted for use with any suitable patient. Patients may include animals or humans of any suitable size. However, embodiments of the invention are especially useful when the patients are infants such as neonates. Although neonatal patients are discussed in detail below, it is understood that embodiments of the invention are not limited to endotracheal tubes and methods for intubating neonates.

One embodiment of the invention is directed to an endotracheal tube comprising: a) a tubular member including a distal end and a proximal end; and b) a plurality of visually distinct regions at a proximal portion of the tubular member, wherein each of the distinct regions comprises a respectively different color.

Another embodiment of the invention is directed to a method of inserting an endotracheal tube in a patient, the method comprising: a) obtaining an endotracheal tube comprising a tubular member including a distal end and a proximal end, and a plurality of visually distinct regions at a proximal portion of the tubular member, wherein each of the distinct regions comprises a respectively different color; b) inserting the distal end of the endotracheal tube into a patient; and c) aligning one visually distinct region of the visually distinct regions with an anatomical structure of the patient.

Another embodiment of the invention is directed to a method of inserting an endotracheal tube in a patient, the method comprising: a) obtaining an endotracheal tube comprising a tubular member including a distal end and a proximal end, and a plurality of visually distinct regions at a proximal portion of the tubular member, wherein each visually distinct region is spaced from other visually distinct regions; b) inserting the distal end of the endotracheal tube into a patient; c) aligning one visually distinct region of the visually distinct regions with the upper gingival ridge (the upper gum) of the patient; and d) securing the endotracheal tube to the patient so that the one visually distinct region is localized with respect to the upper gingival ridge.

In preferred embodiments of the invention, the distinct regions on the endotracheal tube are brightly colored lines. During intubation, one of the lines is selected and localized at, for example, a fixed anatomical location such as the upper gingival ridge. The depth of insertion for the endotracheal tube can be easily determined by viewing the selected and localized line, even though the distal end of the endotracheal tube is not visible to the caregiver. Moreover, the brightly colored lines are more easily discernable to the caregiver than, for example, mono-colored markings such as black printed numbers. Accordingly, by using embodiments of the invention, the occurrence of complications from improper intubation such as RMSBI is reduced.

These and other embodiments of the invention are described in further detail below with reference to the Figures and the Detailed Description.

DETAILED DESCRIPTION

In 1971, Kuhns and Poznanski reported that 18 of 36 (50%) newborn infants treated with assisted ventilation had RMSBI found on their chest radiographs. Kuhns and Poznanski suggested that small black numbers be imprinted on the endotracheal tube to judge the proper depth of insertion and avoid RMSBI. The present inventors investigated whether such markings on endotracheal tubes reduced the incidence of RMSBI. As noted in the Example Section below, the inventors performed both a retrospective review and a prospective study (a randomized clinical trial using the new invention) of RMSBI in their institution. The results of the review and the prospective study showed that intubations performed in the delivery room, and prolonged intubation required for assisted ventilation, still carried a risk for RMSBI that was 20% or higher even using endotracheal tubes with the numbered markings suggested by Kuhns and Poznanski. Although this percentage is lower than the 50% incidence reported by Kuhns and Poznanski in 1971, this occurrence is still unacceptable because of the morbidity or mortality associated with RMSBI. Other caregivers may have considered this reduction in RMSBI reasonable because more extremely preterm infants receive care today. The inventors, however, thought additional improvements in endotracheal tube design might further reduce the incidence of RMSBI.

The present inventors determined that there are a number of reasons why RMSBI occurs in neonates. First, there has been difficulty in accurately determining whether the distance from the lip to the tip of the endotracheal tube will achieve a suitable mid-tracheal position during oro-tracheal intubation (cited in Kuhns et al.; Tochen M. L., Orotracheal intubation in the newborn infant: a method for determining depth of tube insertion, *J Pediatr* 1979;95:1050–1; and Kattwinkel J., *Textbook of Neonatal Resuscitation*. 4th ed., Elk Grove Village: American Academy of Pediatrics and American Heart Association; 2000, p. 5–19). Second, the methods for securing endotracheal tubes vary. Based on the method used to secure the tube, there is a greater or lesser likelihood of having a dislodged and malpositioned endotracheal tube (cited in Brown, M. S., Prevention of accidental extubation in newborns. *Am J Dis Child* 1988;142:1240–3). Third, in the past, the upper lip has been used to secure the endotracheal tube during oro-tracheal intubation. While the upper lip is suitable for attachment, the upper lip is a mobile structure that can slip back and forth (i.e., a yo yo effect) and cause the downward displacement of the endotracheal tube into the right mainstem bronchus. Lastly, extremely preterm infants have a very short distance between the larynx and the carina as mentioned earlier. The reduced anatomical distance predisposes these preterm infants to RMSBI.

Different strategies involving endotracheal tube design have been described to prevent RMSBI. For example, based on studies by Kuhns et al. and Loew et al. (cited in Loew A. and Thibeault D. W., A new and safe method to control the depth of endotracheal intubation in neonates, *Pediatrics* 1974;54:506–8), endotracheal tube manufacturers have placed numbers in centimeters and vocal cord identifying lines, respectively, on neonatal endotracheal tubes.

Loew et al. described a method to control the depth of insertion during the intubation procedure by advocating the placement of a black safety line proximal to the tip of the endotracheal tube. Safety lines at the end of the endotracheal tube have become known as "vocal cord localizers", and the lines are placed at different distances from the endotracheal tube tip based on the weight of the infant. These safety lines are to be placed at the level of the larynx to prevent RMSBI. During oro-tracheal intubation, however, the process of securing the endotracheal tube to the upper lip means the caregiver no longer has a view of the vocal cord localizer, and thus the tube may become displaced either during the process of securing the tube to the lip or during subsequent prolonged intubation and assisted ventilation. The safety lines or "vocal cord localizers" are never visible to the caregiver after intubation and the caregiver may not know that the endotracheal tube is malpositioned or has unexpectedly moved.

Kuhns et al. suggested that manufacturers place centimeter marks along the endotracheal tube. More specifically, numbers are displayed on the tube in centimeters all in the same color (e.g., black). However, the numbers are small and difficult to see during the process of securing a neonatal endotracheal tube. The numbers are so small that some caregivers have commented that they use the letters in the imprinted manufacturer's name as a point of reference (instead of the numbers) when securing the endotracheal tube to the patient. Also, once the endotracheal tube is secured to the lip, the centimeter numbers on the endotracheal tube are hard to see either because the numbers are underneath the tape used to secure the tube or the numbers are inside the mouth of the patient.

The present inventors have determined that a plurality of distinctly identifiable regions (colored lines) on the endotracheal tube makes it easier for a caregiver to determine the proper insertion depth for the endotracheal tube. In preferred embodiments, the plurality of identifiable regions is a plurality of colored distinct regions (e.g., a plurality of brightly colored lines placed proximally on the endotracheal tube at defined distances from the tip). Each distinct region within the plurality of distinct regions can have the same or different pattern. In embodiments of the invention, the plurality of identifiable regions is closer to the proximate end (near the opening of the mouth) of the endotracheal tube than the distal end of the endotracheal tube (near the middle part of the trachea).

As noted, the distinct identifiable regions can be colored different colors so that each distinct region corresponds to a particular depth of insertion. When the endotracheal tube is used, an appropriate region for the patient can be aligned with and then localized to an anatomical structure in the patient. A preferred anatomical structure in the proximal airway is the upper gingival ridge (i.e., the upper gum). The caregiver can easily see a distinct and desired region of the endotracheal tube for placement next to the upper gum during the intubation process and also during prolonged intubation.

The distinct regions are preferably brightly colored solid lines. Each brightly colored line may correspond to a predetermined depth of intubation. For example, the proximal lines placed on an endotracheal tube can be linked to an already established principle associated with neonatal intubation. For example, the "Rule of 1, 2, 3/7, 8, 9" could be used to locate the lines on the endotracheal tube. This "Rule" implies that: if the baby has a weight of about 1 kg, the intubation depth is about 7 cm from the tip of the endotracheal tube to the upper lip; infants weighing close to about 2 kg have the endotracheal tube placed at 8 cm; and infants weighing about 3 kg have the endotracheal tube located at about 9 cm. This "Rule" is the guideline cited in the Textbook of Neonatal Resuscitation published by the American Academy of Pediatrics and American Heart Association. "The Rule" as stated in the Textbook of Neonatal Resuscitation says "adding 6 to the baby's weight in kilograms will give you a rough estimate of the correct distance from the tube tip to the vermillon border of the upper lip".

As noted above, a distinct region on the endotracheal tube is preferably localized with respect to the upper gingival ridge. While the "Rule" can be an indicator for the depth of insertion when the lip is used as a localizing structure, some allowance may be needed for the shorter distance from the tip of the endotracheal tube to the middle of the upper gingival ridge. For example, measurements performed by the inventors have indicated that about 0.5 centimeters could be subtracted from the 7, 8, 9 rule. Thus, brightly colored, circumferential lines could be placed at about 6.5, about 7.5, about 8.5 and about 9.5 centimeters from the distal end of the endotracheal tube. One of these lines on the endotracheal tube could be placed beside the midline of the upper gum based on the infant weighing 1, 2, 3 or 4 kg, respectively. Using this new method to judge the depth of insertion of the neonatal endotracheal tube, RMSBI during the initial intubation, subsequent securing, and during prolonged assisted ventilation of neonates can be avoided or reduced.

I. Endotracheal Tubes

Figure 2:
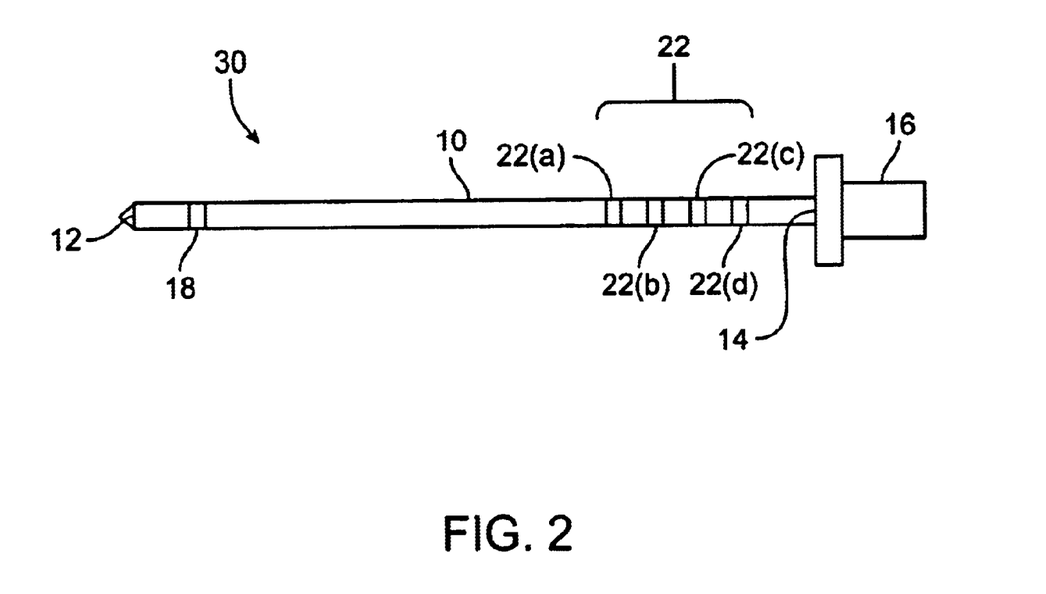
FIG. 2 shows a side view of an endotracheal tube according to an embodiment of the invention.

An endotracheal tube 30 according to an embodiment of the invention is shown in FIG. 2. The endotracheal tube 30 includes a tubular member 10 with a distal end 12 and a proximal end 14. The distal end 12 is beveled in most embodiments. An endotracheal tube adapter 16 (i.e., a connector to an assisted ventilation device) is at the proximal end of the tubular member 10. The endotracheal tube adapter 16 can be coupled to a gas source (e.g., an oxygen and air mixture or an anesthetic gas source) and provides treatment via the endotracheal tube 30. Depending on the design, the adapter 16 is internally or externally inserted into/onto the tubular member 10 respectively (or could another suitable coupling mechanism), so that the endotracheal tube adapter can be attached to, e.g., a gas line.

The tubular member 10 may comprise any suitable dimensions. Preferably, the parts of the endotracheal tube may be sized so that they are configured for use with an infant (e.g., a neonate). In these embodiments, the external diameter of the tubular member 10 can be about 20, or even about 10 millimeters or less. The length of the tubular member 10 can be about 20 centimeters, or even about 10 centimeters or less. In other embodiments, the tubular member 10 may be sized so that it can be used with an adult so that the tubular member 10 would be much larger than these dimensions.

The tubular member 10 may comprise any suitable material. For example, the tubular member 10 may include a flexible medical grade plastic material. Exemplary materials include polyvinyl chloride, silicone elastomer, polyurethanes, etc.

In the illustrated example, a plurality of distinct regions 22 is on the tubular member at a proximal portion thereof. The proximal portion of the tubular member 10 having the plurality of distinct regions can be close to the proximal end of the tubular member 10, and generally includes the region of the endotracheal tube that is near to the entrance to the patient (e.g., near the mouth).

In this example, a first distinct region 22(*a*), a second distinct region 22(*b*), a third distinct region 22(*c*), and a fourth distinct region 22(*d*) are included in the plurality of distinct regions 22. Although four distinct regions 22(*a*), 22(*b*), 22(*c*), 22(*d*) are shown in the endotracheal tube 30 shown in FIG. 2, in other embodiments, there may be more or less distinct regions in the plurality of distinct regions 22. For example, in some embodiments, the plurality of distinct regions 22, may include at least 2 or more than 2 distinct regions.

Each distinct region 22(*a*), 22(*b*), 22(*c*), 22(*d*) has a different color. As used herein, "different colors" can include different shades of the same color (e.g., different hues as distinguished by their chroma, intensity, saturation, etc.) and distinctly different colors. Examples of suitable colors, without limitation, include red, blue, yellow, cyan, magenta, black, purple, pink, green, orange, gray, etc. In one example, the four distinct regions 22(a), 22(b), 22(c), 22(d) respectively comprise red, green, yellow, and blue. In another example, the plurality of distinct regions may include three distinct regions of different color. For instance, an exemplary endotracheal tube may include pink, red, and brick colored lines.

Each distinct region 22(a), 22(b), 22(c), 22(d) is spaced a predetermined distance from the distal end 12 of the endotracheal tube. In some embodiments, the distal regions 22(a), 22(b), 22(c), 22(d) are respectively spaced about 6.5–7.0 cm, about 7.5–8.0 cm, about 8.5–9.0 cm, and about 9.5–10 cm from the distal end 12 of the endotracheal tube 30. For example, referring to FIG. 2, the distal regions 22(a), 22(b), 22(c), 22(d) can be respectively spaced at 6.5 cm, at 7.5 cm., at 8.5 cm, and at 9.5 cm from the distal end 12 of the endotracheal tube 30.

In embodiments of the invention, the distinct regions 22(a), 22(b), 22(c), 22(d) are spaced at any suitable distance from each other. In some embodiments, each distinct region 22(a), 22(b), 22(c), 22(d) can be spaced about 1 cm or less from an adjacent distinct region.

A suitable distinct region (e.g., either 22(a), 22(b), 22(c), or 22(d)) is used as a reference point for determining the proper depth of insertion of the endotracheal tube 30. Thus, the spacing between regions may be determined by using the central point of each distinct region 22(a), 22(b), 22(c), 22(d). These central points may be used to determine the spacing of the distinct regions from each other and from the distal end 12 of the endotracheal tube (30).

Each distinct region 22(a), 22(b), 22(c), 22(d) is preferably in the form of a continuous line (so it can be viewed from any point when looking into the mouth at the upper gum) that wraps around the tubular member. The line may be any suitable width. For example, in some embodiments, the width of each distinct region 22(a), 22(b), 22(c), 22(d) may be about 1 cm or less, or about 0.5 cm or less (e.g. 0.25 cm). Generally, the lower limit for the width of each distinct region 22(a), 22(b), 22(c), 22(d) may be such that each distinct region 22(a), 22(b), 22(c), 22(d) is easily discernable with the naked eye while at an arm's length distance.

Each distinct region 22(a), 22(b), 22(c), 22(d) could be formed on or embedded into the tubular member 10. In another embodiment, suitable dyes or pigments are embedded into the tubular member 10 at distinct region 22(a), 22(b), 22(c), 22(d) to form identifiable lines. This method is preferred. In other embodiments, the distinct regions 22(a), 22(b), 22(c), 22(d) could be printed onto the tubular member 10 (e.g., with paint, ink, etc.).

Each different distinct region 22(a), 22(b), 22(c), 22(d) in the plurality of distinct regions 22 may comprise a different color that represents a certain distance from the distal end 12 (i.e., the tip) of the endotracheal tube 30. When intubating a patient, one of the distinct regions 22(a), 22(b), 22(c), 22(d) may be selected according to the patient's size, weight, or other predetermined criteria. Then, the selected distinct region can be aligned with an anatomical structure in the patient. The endotracheal tube 30 may then be secured to the patient so that the selected distinct region is localized with respect to the anatomical feature. Various securing steps are described in further detail below.

An optional safety marking or "vocal cord localizer" 18 may also be on the tubular element 10. The optional safety marking may be aligned with the patient's vocal cords when the endotracheal tube 30 is inserted into the trachea via a patient's mouth or nose. In the illustrated example, the safety marking 18 is closer to the distal end 12 of the tubular member 10 than the proximal end 14 and is in the form of a black continuous or discontinuous line that wraps around the tubular member 10. The safety marking 18 usually comprises a different color (i.e., black) compared to the colors of the four distinct regions 22(a), 22(b), 22(c), 22(d). For example, the color of the safety marking 18 can be black, while the colors of the four distinct regions 22(a), 22(b), 22(c), 22(d) can be blue, green, yellow, and red. The distance between the safety marking 18 and the distal end 12 can vary based on the range of patients that would be using the endotracheal tube 30. As shown, the remainder of the tubular member 10 may be substantially free of marked regions (e.g., free of centimeter numerical markings).

Various modifications can be made to the endotracheal tube 30 shown in FIG. 2 while still being within the scope of the invention. For example, an inflatable cuff (not shown) could be provided near the distal end 12 of the tubular member 10. The inflatable cuff would be beyond the safety marking and closer to the endotracheal tube tip. The inflatable cuff, not used in neonates because it can cause injury to the trachea, is used in older patients to prevent leakage of inspired gases when a breath is given via the ventilator. A pilot tube (a second mini-tube imbedded in the wall of the endotracheal tube and not shown) is in communication with the inflatable cuff. This pilot tube is used to inflate or deflate the cuff as desired. Also, such inflatable cuffs may be used to prevent the endotracheal tube from being dislodged from the patient during intubation and/or can prevent the regurgitation and aspiration of stomach contents into the patient's lungs.

II. Methods for Using Endotracheal Tubes

Embodiments of the invention also relate to methods for intubating patients. In one embodiment, the method comprises obtaining an endotracheal tube comprising a tubular member including a distal end and a proximal end, and a plurality of visually distinct regions closer to the proximal end than the distal end. Each visually distinct region is spaced from other visually distinct regions, and each of the distinct regions comprises a respectively different color. The endotracheal tube may have any of the features in the embodiments described above.

Prior to inserting the endotracheal tube into the patient, one of the distinct regions is selected for a particular patient. As will be explained in further detail below, the selected distinct region is eventually localized with respect to an anatomical structure in the patient.

Any suitable parameter may be used to determine which distinct region to select. For example, in some embodiments, the patient's weight may be determined in order to determine which of the distinct regions is to be aligned with the fixed, anatomical structure of the patient. As noted above, the 1, 2, 3/7, 8, 9 rule (or a modification thereof) may be used. Illustratively, blue, green, and red colored distinct regions may be spaced about 7,8, and 9 centimeters from the distal end of the endotracheal tube and used for infants weighing 1,2, or 3 kilograms, respectively. According to the "Rule" of 1, 2, 3/7, 8, 9, these marks would be localized to the upper lip rather than the upper gum. For example, if the patient weighs about 1 kg, then the blue distinct region would be associated with a 7-centimeter line that measures the distance from tip of the endotracheal tube to the upper lip. The shorter distance to the upper gum (e.g., 6.5 cm) from the endotracheal tube tip is conceptually part of the invention and is the reason why 0.5 centimeter is subtracted from the "Rule" of 1, 2, 3/7, 8, 9. Using the upper gum rather than the upper lip, avoids the mobility associated with the lip when judging the depth of insertion.

After selecting one of the distinct regions, the distal end of the endotracheal tube is inserted into, for example, the nose or mouth of the patient. If the endotracheal tube is inserted into either the nose or mouth, intubation aids such as laryngoscopes or stylettes can be used to help insert the endotracheal tube into the patient.

After inserting the distal end into the patient's trachea, the selected distinct region is aligned with an anatomical structure of the patient. After aligning the endotracheal tube with the anatomical structure, the endotracheal tube is secured to (e.g., attached) the patient to localize the selected distinct region with respect to the anatomical structure.

Any suitable anatomical structure may be used as a reference point. The anatomical structure of the patient could be, for example, the patient's upper lip or the patient's upper gum. Preferably, the anatomical structure should be a fixed anatomical structure such as the upper gum. Movable anatomical structures such as the upper lip may have a tendency to move the endotracheal in and out during prolonged intubation. In very preterm human infants, and to a lesser extent in older patients, the to and fro movement of the endotracheal tube increases the risk of RMSBI.

Figure 3:
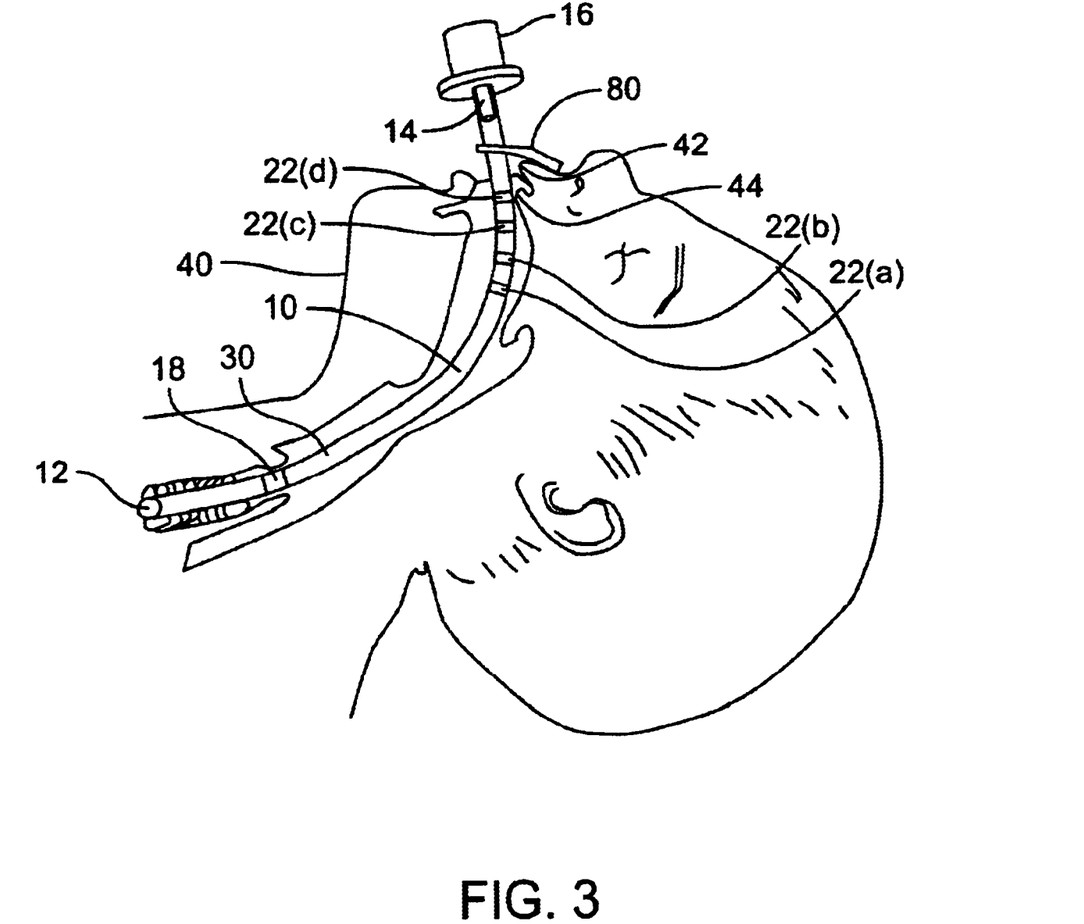
FIG. 3 shows a diagram of an endotracheal tube according to an embodiment of the invention as it is being used in a newborn infant.

FIG. 3 shows how an endotracheal tube 30 according to an embodiment of the invention could be used in a patient 40. In FIG. 3, like numerals designate like elements as shown in FIG. 2. Referring to FIG. 3, a brightly colored distinct region 22(d) (a line) on the endotracheal tube 30 has been aligned with the patient's upper gum line 44. In other embodiments, the brightly colored distinct region 22(d) could be aligned with the patient's upper lip 42.

Referring to FIG. 3, the insertion distance is based on weight in kilograms, and the colors of the lines assigned to the different weights can be as follows: a 4 kg infant has a 9.5 cm distance of insertion (endotracheal tube tip to upper gum) and the colored distinct region 22(d) is orange, a 3 kg infant has a 8.5 cm distance of insertion and the distinct region 22(c) is colored green, a 2 kg infant has a 7.5 cm distance of insertion the distinct region 22(b) is colored blue, and a 1 kg infant has a distance of insertion of 6.5 cm and the distinct region 22(a) is colored red. As shown in FIG. 3, the distinct regions 22(a), 22(b), 22(c), 22(d) may be in the form of colored lines that wrap circumferentially around the endotracheal tube 30. The distances for the depth of insertion are measured from the upper gum line 44 to the distal end 12 of the endotracheal tube 30. At these distances, the distal end 12 of the endotracheal tube 30 is accurately positioned at or near the mid-trachea. In FIG. 3, the black safety line 18 is localized adjacent to the patient's vocal cords. This localization of the safety line also indicates that the endotracheal tube 30 is properly positioned.

After aligning the selected distinct region 22(d) with the gum line 44, a securing device 80 may be used to secure the endotracheal tube 30 to the patient 40. In some embodiments, the securing device could simply be tape that is sutured (or otherwise attached) to the endotracheal tube 30. Other devices for attaching endotracheal tubes to patients could be used. One type of device used in neonates is called NeoBar®. This is a rigid bar across the mouth that is affixed to each cheek. The endotracheal tube is attached to the bar and not the lip. This device could avoid the problem of back and forth movement of the lip and displacement of the endotracheal tube. Another device used to secure endotracheal tubes in newborn infants, NEO-fit™, uses cheek and lip pads to which a rapid release and refit Velcro strap is attached to the endotracheal tube. These devices are commercially available.

EXAMPLE

The present inventors performed two studies to ascertain the incidence of RMSBI in intubated neonates. Specifically, a retrospective study and a prospective study were performed.

Retrospective Study

A first phase of this study retrospectively reviewed the incidence of RMSBI at a particular medical center. This first phase was conducted before evaluating the new endotracheal tube design according to embodiments of the invention. The retrospective review was for the years 1996, 1997, and 1998. A database identified all intubated infants. Charts of these patients were abstracted for demographic information and reports of all chest radiographs. The protocol in the NICU (neonatal intensive care unit) for performing chest radiographs kept the head in the midline position with the arms extended beside the head. During the 1996 through 1998 period, the endotracheal tube had the same localizing marks as standard neonatal endotracheal tube in use today. This endotracheal tube was used later for control infants in the prospective study. Information from the chart review established the incidence of RMSBI during the initial intubation and the occurrence of RMSBI during prolonged intubation and assisted ventilation, excluding any RMSBI cases that were identified because of re-intubation. Demographic information was correlated with RMSBI during assisted ventilation to determine risk factors associated with its cause.

Prospective Study

The second phase of this study was conducted over about a 17-month period. Inclusion criteria included newborn infants regardless of birth weight and gestational age that required oro-tracheal intubation and for whom informed consent was obtained. Exclusion criteria included newborn infants with head, neck, or thoracic anomalies. Infants were also excluded at the discretion of the attending neonatologist.

The prospective study randomly assigned infants to one of two groups based on the type of endotracheal tube used and the procedure utilized to ascertain the depth of insertion during oro-tracheal intubation. Group 1 used neonatal endotracheal tubes with single-colored (black) centimeter marks and the vocal cord localizer lines (also black). Subjects in Group 1 were enrolled during the odd numbered months of the study. Group 2 had brightly colored lines placed circumferentially at 6.5, 7.5, 8.5 and 9.5 cm from the tip of the endotracheal tube. These subjects were enrolled during the even numbered months of the study. The lines on the endotracheal tube consisted of non-toxic and tightly adherent tape that was 0.25 centimeters wide. Tubes with the adherent colored tape were prepared and gas sterilized before use.

The following procedures were utilized in the study. Group 1 used the upper lip as a reference point and "The Rule" (cited in Tochen M. L.; and Kattwinkel J.) for inserting the endotracheal tube to the desired depth (Table 1).

TABLE 1

Oro-tracheal Tube Insertion:
Distance from Lip-to-Tip Vs. Upper Gum Line-to-Tip

| Weight, kg | Mid-Line Depth of Orotracheal Tube Insertion | |
|---|---|---|
| | (cm. from upper lip)* | (cm. from upper gum line) |
| 1† | 7 | 6.5 |
| 2 | 8 | 7.5 |
| 3 | 9 | 8.5 |
| 4 | 10 | 9.5 |

*Textbook of Neonatal Resuscitation (published by American Academy of Pediatrics)
†Babies weighing <750 g may require a 6 cm insertion from tip-to-lip. This recommendation was considered when inserting endotracheal tube into infants below this weight.

The investigator responsible for an individual subject decided the insertional depth in centimeters based on either an estimated fetal weight or the actual birth weight. An estimated fetal weight was based on the average weight for the calculated gestational age of the fetus that was determined by either the last menstrual period and/or a fetal ultrasound examination. Following insertion of the endotracheal tube, the tube was secured to the upper lip using a previously described method (cited in Gregory G. A., Respiratory care of newborn infants. *Pediatr Clin North Am*, 1972;19:311–24). The depth of insertion was based on the single-colored centimeter mark that was permanently affixed to the tube and was localized adjacent to the upper gum.

For Group 2, the estimated fetal weight or actual birth weight was also used to determine the depth of insertion, but the depth of insertion was reduced by 0.5 centimeters (Table 1). The reason for the reduction in the depth of insertion is that a brightly colored line was located adjacent to the midline of the upper gingival ridge based on birth weight rather than locating the depth of insertion to the lip. In other words, this procedure differed from locating the centimeter marks to the upper lip as was the method used for Group 1.

The taping method for securing the endotracheal tube to the lip was the same in Group 1 and Group 2. This method of fixation was also used to secure endotracheal tubes during 1996 through 1998. After intubation, initial and subsequent chest radiographs were performed with the endotracheal tube in a midline position and the neck located in a neutral position without flexion, extension, or rotation because such movements can change the position of the endotracheal tube in the trachea (cited in Donn S. M. and Kuhns L. R., Mechanism of endotracheal tube movement with change of head position in the neonate, *Pediatr Radiol* 1980;9:37–40). An attending pediatric radiologist that did not know the group assignments confirmed the anatomical position of all endotracheal tube placements. Subsequent chest radiographs were done depending on the patient's clinical status and at the discretion of the attending neonatologist. During the course of assisted ventilation, the nurses, respiratory care practitioners, or physicians assessed the proper location of the endotracheal tube by examining either the centimeter marks on the tube inside the mouth (Group 1) or the brightly colored lines placed at the upper gingival ridge (Group 2).

As noted, in the study, neonates in Group 2 were intubated with endotracheal tubes with brightly colored lines located at their upper gingival ridges (see FIG. 3). During the study, caregivers could easily elevate the lip at the corner of the mouth and visualize that the colored line remained in its proper position at the upper gum. Taping the endotracheal tube of infants assigned to Group 1 nearly always obscured the visual assessment of the centimeter marks at the upper lip. After the study had ended, and per comments by the caregivers, black centimeter numbers on the tube were difficult to visualize inside of the mouth, while the brightly colored lines easily allowed an assessment of the depth of endotracheal tube insertion.

The following characteristics were recorded in both groups: birth weight, gestational age, gender, depth of insertion after the first intubation, adjustments made to initial endotracheal tube placement, and abnormal position of the endotracheal tube on follow-up chest radiographs while the subjects were intubated.

Statistical Analysis

SPSS 9.0 commercially available from SPSS, Inc. was used for statistical analysis of the results. Parametric or non-parametric statistical analysis was performed as appropriate (cited in Glantz S. A., *Primer of Biostatistics*, New York: McGraw-Hill; 1997, p. 403–424).

Results

Retrospective Study

The demographic findings for the retrospective part of the study are summarized in Table 2.

TABLE 2

Demographic Findings in the Retrospective Study (1996–1998)

| | n | (% of n) |
|---|---|---|
| Number of NICU Admissions | 1475 | 100 |
| Number of intubated Infants | 447 | 30 |
| Gestational Age (wks)* of Intubated Infants | | |
| 23–26 | 60 | 13 |
| 27–29 | 104 | 23 |
| 30–33 | 84 | 19 |
| 34–36 | 87 | 20 |
| 37–42+ | 112 | 25 |
| Gender | | |
| Male | 237 | 53 |
| Female | 210 | 47 |
| Number of infants intubated in: | | |
| 1) Delivery Room | 238 | 53 |
| 2) NICU | 209 | 47 |
| Number of RMSBI when performed in: | | |
| 1) Delivery Room | 46 | 19 |
| 2) NICU | 44 | 21 |

*Birth weight range was from 455 to 4185 grams.

Figure 4:
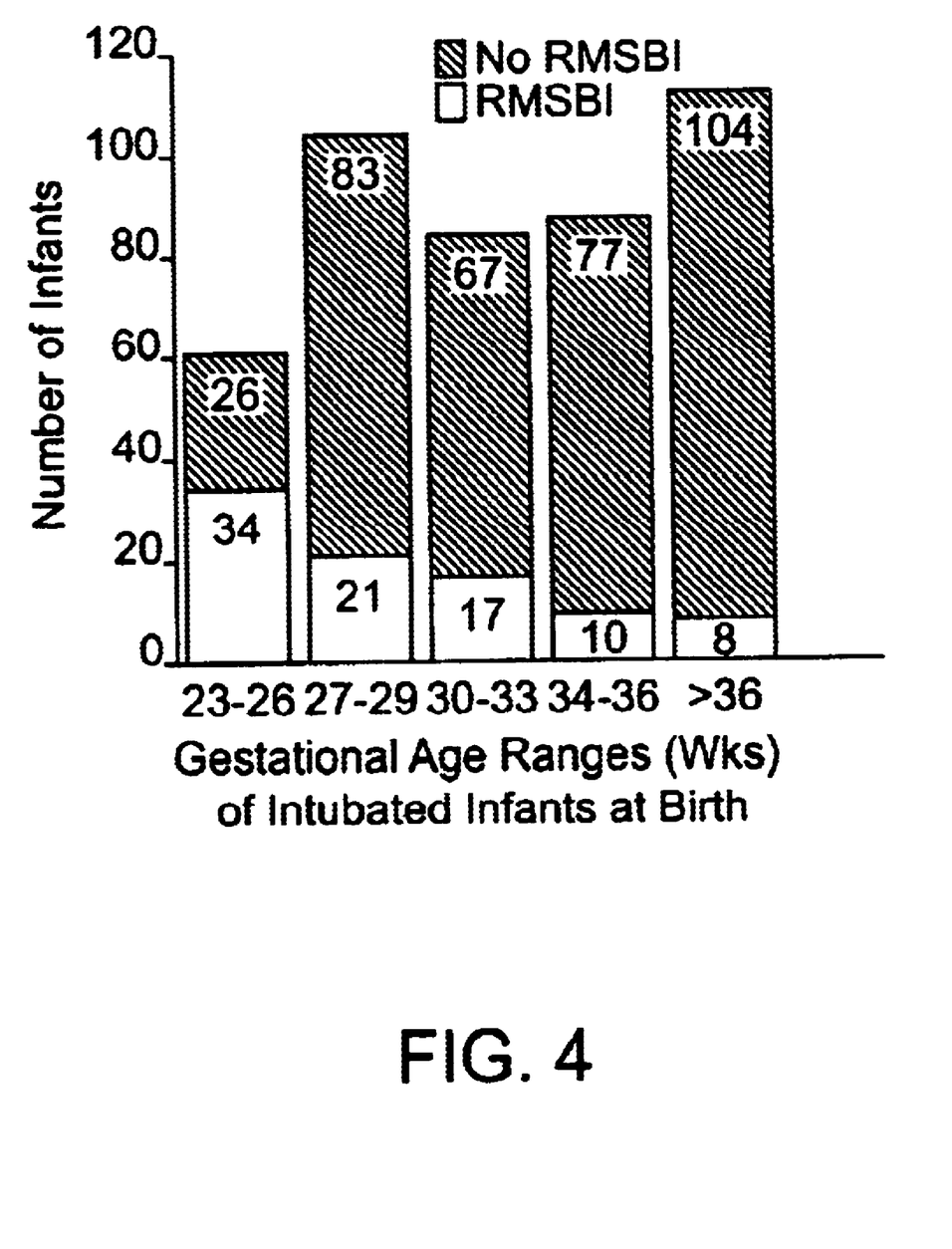
FIG. 4 shows a bar graph of the number of intubated infants that do or do not have right mainstem bronchial intubation (RMSBI) as a complication of their size at a given gestational age (weeks after conception).

FIG. 4 shows the relationship between gestational age and the incidence of right mainstem bronchial intubation (RMSBI) in the retrospective study. The gestational age ranges at birth are shown on the "x" axis and the number of subjects that did or did not have RMSBI is displayed on the "y" axis. The lighter bars represent the infants with RMSBI and the solid bars indicate infants that did not have RMSBI.

Whether intubations occurred in the delivery room or the neonatal intensive care unit, the overall incidence of RMSBI was approximately 20% as compared to earlier studies by others. FIG. 4 shows that the youngest gestational age category, 23–26 weeks, had a higher risk of RMSBI than did gestational age categories greater than 26 weeks ($\chi^2$=54.93, P<0.001). When infants born at 23–26 weeks and 27–29 weeks of gestation were compared to infants born at ≧37 weeks of gestation, there was also a higher risk of RMSBI in the two younger gestational age categories, respectively ($\chi^2$=49.27, P<0.001 and $\chi^2$=6.81, P=0.009, respectively). An analysis of RMSBI during prolonged assisted ventilation also revealed that the longer assisted ventilation was used, the more likely RMSBI was to occur. This analysis did not include RMSBI that occurred during re-intubation caused by an unscheduled extubation.

Prospective Study

Table 3 shows the demographic findings of subjects in the prospective study. While the sample population was predominately Caucasian males, multivariate analysis between groups revealed no statistical difference in regards to gender, gestational age, birth weight, or race. Levene's Test of Equality of Error Variances was not significant (P>0.05) and equal variances in the population were assumed between the two groups.

TABLE 3

Demographic Findings of Infants Assigned to Group 1 (No Colored Lines on the Endotracheal Tube) and Group 2 (Colored Lines Proximally Placed on the Endotracheal Tube)

|  | Group 1 (n = 31) | | Group 2 (n = 31) | |
| --- | --- | --- | --- | --- |
|  | n | (% of n) | n | (% of n) |
| Gestational Age (wks)* | | | | |
| 23–26 | 2 | 6 | 5 | 16 |
| 27–29 | 7 | 23 | 8 | 26 |
| 30–33 | 8 | 26 | 9 | 29 |
| 34–36 | 3 | 10 | 5 | 16 |
| 37–42 | 11 | 35 | 4 | 13 |
| Gender | | | | |
| Female | 12 | 39 | 13 | 42 |
| Male | 19 | 61 | 18 | 58 |
| Race | | | | |
| Caucasian | 28 | 90 | 25 | 80 |
| African Americans | 0 | 0 | 3 | 10 |
| Hispanic | 3 | 10 | 3 | 10 |

*Birth weight range was from 567 to 4100 grams.

Of the 62 subjects in the prospective study, none had RMSBI noted on the initial chest radiograph. Five of 31 subjects in Group 1 had the tip of the endotracheal tube at or above the clavicle on the initial chest radiograph (high placement). These endotracheal tubes required re-adjustment to the mid-trachea. All subjects in Group 2 (colored lines placed at the upper gum) had the tip of the endotracheal tube in a satisfactory intra-tracheal position, and no adjustments in position were needed.

Figure 5:
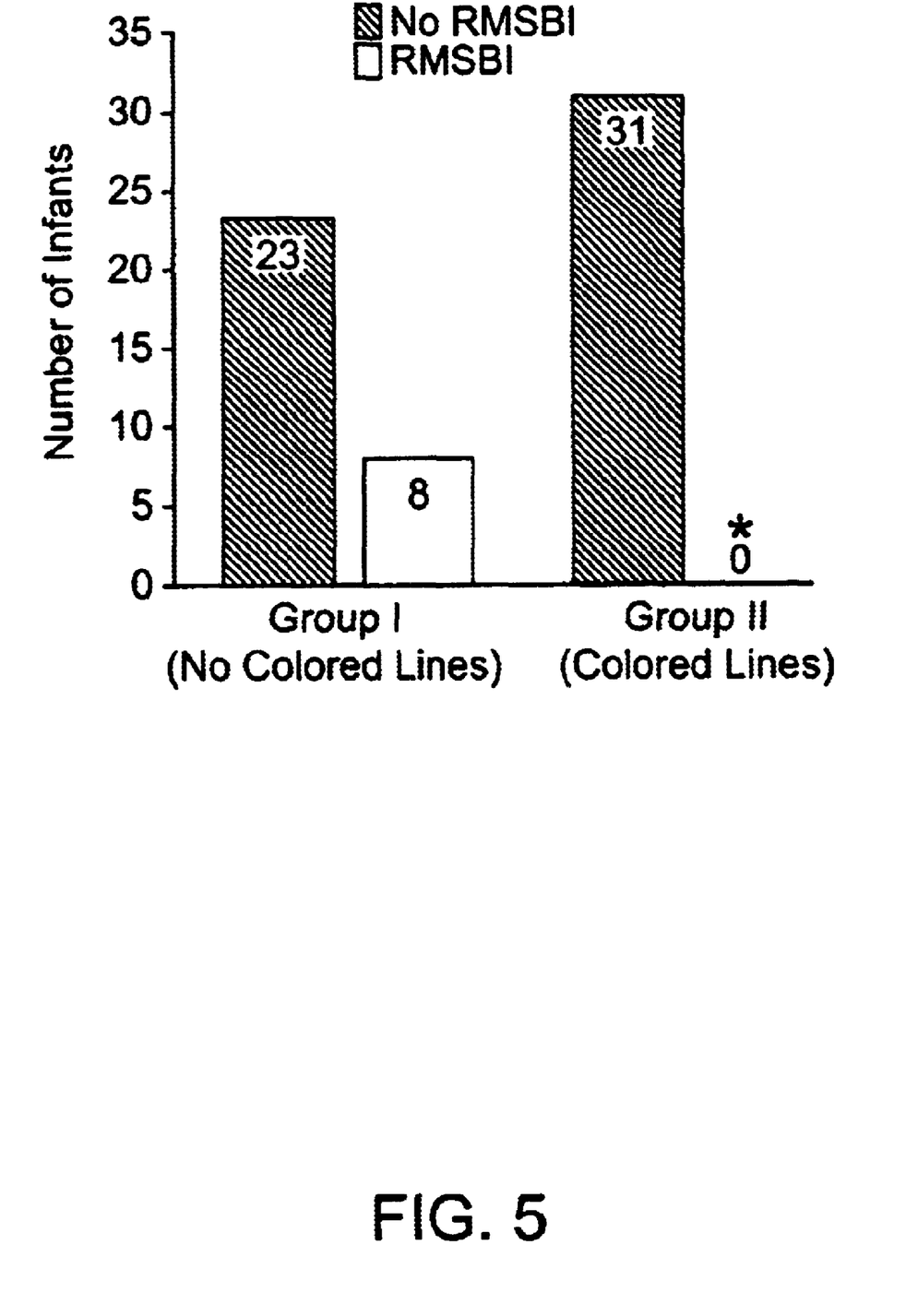
FIG. 5 shows a bar graph of a controlled clinical trial that had one group of newborn infants use a standard endotracheal tube during intubation (Group I), while a second group of infants (Group II) had the newly invented endotracheal tube inserted during intubation. The graph shows that the new endotracheal tube design eliminated right mainstem bronchial intubation (RMSBI) during prolonged assisted ventilation of newborn infants randomly assigned to Group II.

FIG. 5 shows the number of subjects in both groups that had RMSBI during subsequent ventilator care. This information only includes RMSBI that occurred while infants were on the ventilator. It does not include RMSBI that may have occurred during re-intubation while an infant was receiving ventilatory support. In Group 1, 8 of 31 subjects or 26% had RMSBI, while none of the 31 newborn infants in Group 2 had RMSBI identified on chest radiography ($x^2$= 34.13, P<0.01).

The strength of the relationship between RMSBI and the new endotracheal tube design, as assessed by the effect size index, $\eta^2$, was small with the new endotracheal tube design accounting for 15% ($\eta^2$=15) of the variance. Akin to the retrospective study, RMSBI had an inverse correlation with gestational age at birth and accounted for 85% ($\eta^2$=85) of the variance in RMSBI. The observed power of the prospective study was 0.90. As noted above, Group 1 had endotracheal tubes with the usual markings placed in the trachea and the "Rule of 1, 2, 3/7, 8, 9" was used to determine the desired depth of insertion (e.g., a 1 kg infant would be intubated to a depth of 7 cm from the lip-to-endotracheal tube tip). Group 2 had brightly colored, circumferential lines placed at 6.5, 7.5, 8.5 and 9.5 centimeters from the tip of the endotracheal tube, and the "Rule" was modified so these lines were placed adjacent to the upper gum of infants having birth weights of 1, 2, 3 or 4 kg, respectively.

In this study, the present inventors validated the "Rule of 1, 2, 3/7, 8, 9", but found that the tip of the endotracheal tube might be in a high position using the "Rule". After the initial intubation, 5 of 31 subjects in Group 1 had the endotracheal tube located above the clavicles and endotracheal tube required re-positioning into the mid-trachea. The findings suggested that using a brightly colored line located at the upper gingival ridge avoided a high position of the endotracheal tube during the initial intubation. A brightly colored line placed at the upper gum line also prevented RMSBI during either the initial intubation or subsequent ventilator care.

It was remarkable that no RMSBI occurred in Group 2 during prolonged intubation. The new method to identify the depth of endotracheal tube insertion with colored lines meant the caregivers immediately knew the Group assignment. There was no way to mask the new design in endotracheal tube. Evaluation of the position of the colored line, and correction if it was dislocated, was however essential to study outcome. It is conceivable that medical, nursing, and respiratory care staff were more attentive to displacement of an endotracheal tube when the tube had colored lines on it. As such the Hawthorne effect was a threat to study design validity. Despite this possibility, the present inventors have concluded that using the upper gingival ridge rather than a lip-to-tip assessment for the proper depth of insertion and an endotracheal tube with proximally colored lines means fewer infants will experience RMSBI during assisted ventilation. The randomized clinical trial showed this to be true. Embodiments of the invention appear to be safe and may reduce RMSBI and thus ventilator-related morbidity in neonates. Use of endotracheal tubes of similar design in patients other than neonates may also reduce morbidity and mortality associated with displacement of endotracheal tubes.

While the foregoing is directed to certain preferred embodiments of the present invention, other and further embodiments of the invention may be devised without departing from the basic scope of the invention. Such alternative embodiments are intended to be included within the scope of the present invention. Moreover, the features of one or more embodiments of the invention may be combined with one or more features of other embodiments of the invention without departing from the scope of the invention.

What is claimed is:

1. A method of inserting an endotracheal tube in a patient, the method comprising:
    a) obtaining an endotracheal tube comprising a tubular member including a distal end and a proximal end, and a plurality of visually distinct regions at a proximal portion of the tubular member, wherein each visually distinct region is spaced from other visually distinct regions;
    b) inserting the distal end of the endotracheal tube into a patient;
    c) aligning one visually distinct region of the visually distinct regions with the upper gingival ridge of the patient; and
    d) securing the endotracheal tube to the patient so that the one visually distinct region is localized with respect to the upper gingival ridge.

2. The method of claim 1 wherein the plurality of visually distinct regions comprises a plurality of lines with respectively different colors.

3. The method of claim 1 wherein the plurality of visually distinct regions includes a first distinct region spaced about 6.5–7.0 cm from the distal end, a second distinct region spaced about 7.5–8.0 cm from the distal end, and a third distinct region spaced about 8.5–9.0 cm from the distal end.

4. The method of claim 3 wherein the plurality of distinct regions comprise a plurality of different colors.

5. The method of claim 1 wherein the endotracheal tube is adapted for use with an infant or a premature infant.

6. The method of claim 1 wherein the endotrachael tube further comprises a safety marking closer to the distal end than the proximal end, wherein the safety marking is adapted for alignment adjacent to the patient's vocal cords.

7. The method of claim 1 wherein the tubular member has a length less than about 20 centimeters.

8. The method of claim 1 wherein the patient is an infant.

9. A method of inserting an endotracheal tube in a patient, the method comprising:
   a) obtaining an endotracheal tube comprising a tubular member including a distal end and a proximal end, and a plurality of visually distinct regions at a proximal portion of the tubular member, wherein each of the distinct regions comprises a respectively different color;
   b) inserting the distal end of the endotracheal tube into a patient; and
   c) aligning one visually distinct region of the visually distinct regions with a fixed anatomical structure of the patient, wherein the patient has an upper gum, and wherein the fixed anatomical structure is the upper gum.

10. The method of claim 9 wherein the plurality of visually distinct regions includes a first distinct region spaced about 6.5–7.0 cm from the distal end, a second distinct region spaced about 7.5–8.0 cm from the distal end, and a third distinct region spaced about 8.5–9.0 cm from the distal end.

11. The method of claim 9 wherein the endotracheal tube is adapted for use with an infant or a premature infant.

12. The method of claim 9 wherein the endotracheal tube further comprises a safety marking closer to the distal end than the proximal end, wherein the safety marking is adapted for alignment adjacent to the patient's vocal cords.

13. The method of claim 9 further comprising securing the endotracheal tube to the patient.

14. The method of claim 9 wherein the tubular member has a length less than about 20 centimeters.

15. The method of claim 9 wherein the patient is an infant.

* * * * *